United States Patent
Chamney et al.

(10) Patent No.: US 7,917,202 B2
(45) Date of Patent: Mar. 29, 2011

(54) METHOD AND A DEVICE FOR DETERMINING THE HYDRATION AND/OR NUTRITION STATUS OF A PATIENT

(75) Inventors: Paul Chamney, Herts (GB); Peter Wabel, Darmstadt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 396 days.

(21) Appl. No.: 11/630,967

(22) PCT Filed: Jun. 29, 2004

(86) PCT No.: PCT/EP2004/007023
§ 371 (c)(1),
(2), (4) Date: Dec. 28, 2006

(87) PCT Pub. No.: WO2006/002656
PCT Pub. Date: Jan. 12, 2006

(65) Prior Publication Data
US 2008/0086058 A1   Apr. 10, 2008

(51) Int. Cl.
*A61B 5/05* (2006.01)
*A61B 5/02* (2006.01)
*A61B 5/103* (2006.01)
*A61B 5/117* (2006.01)

(52) U.S. Cl. ......... 600/547; 600/506; 600/507; 600/587

(58) Field of Classification Search ........... 600/547, 600/506, 507, 587
See application file for complete search history.

(56) References Cited

U.S. PATENT DOCUMENTS

| | | |
|---|---|---|
| 5,086,781 A | 2/1992 | Bookspan |
| 5,449,000 A | 9/1995 | Libke et al. |
| 5,807,272 A * | 9/1998 | Kun et al. ............ 600/547 |
| 6,151,523 A * | 11/2000 | Rosell Ferrer et al. ....... 600/547 |
| 6,615,077 B1 * | 9/2003 | Zhu et al. ............ 600/547 |
| 2003/0105411 A1* | 6/2003 | Smallwood et al. ......... 600/547 |
| 2004/0171963 A1* | 9/2004 | Takehara ............ 600/547 |

FOREIGN PATENT DOCUMENTS

| | | |
|---|---|---|
| WO | WO 92/19153 | 11/1992 |
| WO | WO 02/36004 A1 | 5/2002 |
| WO | WO 03/053239 A1 | 7/2003 |

OTHER PUBLICATIONS

Noshiro, M., et al., "Electrical Impedance in the Lower Limbs of Patients with Duchenne Muscular Dystrophy: A Preliminary Study," Medical & Biological Engineering & Computing, Mar. 1993, vol. 31, No. 2, pp. 97-102.

* cited by examiner

*Primary Examiner* — Max Hindenburg
*Assistant Examiner* — Adam J Eiseman
(74) *Attorney, Agent, or Firm* — Jacobson Holman PLLC

(57) ABSTRACT

Monitoring the hydration and/or nutrition status of a patient by bioimpedance. A bioimpedance method and device that makes use of a refined model by which the conductivity contributions from intracellular tissues can be taken better into account to enable an improved assessment of the body composition of a patient with increased accuracy. The intracellular volume (ICV) of a patient is determined by determining an intracellular electrical resistance $R_{mix}$ of the patient and deriving the intracellular volume ICV using $R_{mix}$ by taking into account that a cell of a kind of tissue contributes differently to the electrical resistance $R_{mix}$ of the intracellular volume ICV compared with a cell of a second kind of tissue. The application also relates to a device for carrying out the method according to the invention and to a computer program product to be used on such a device.

20 Claims, 5 Drawing Sheets

Figure 1:
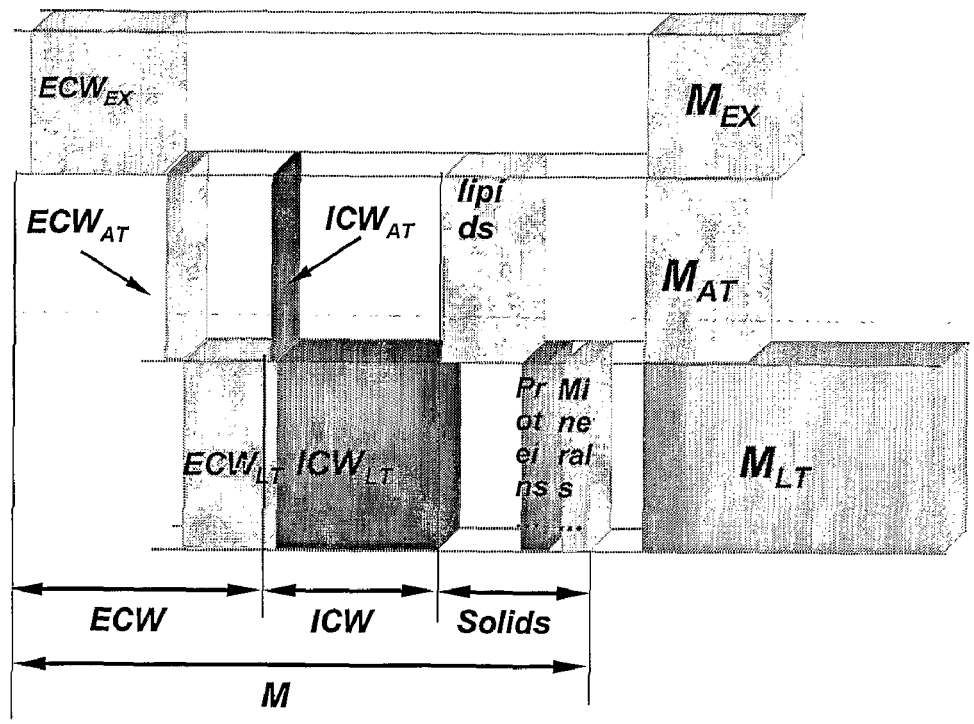

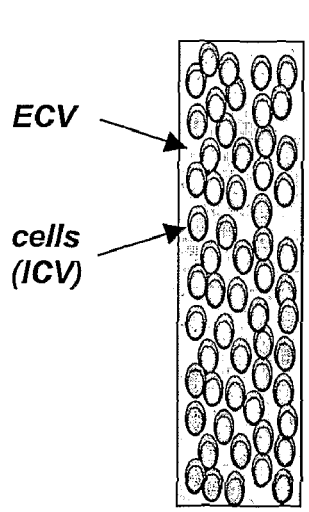
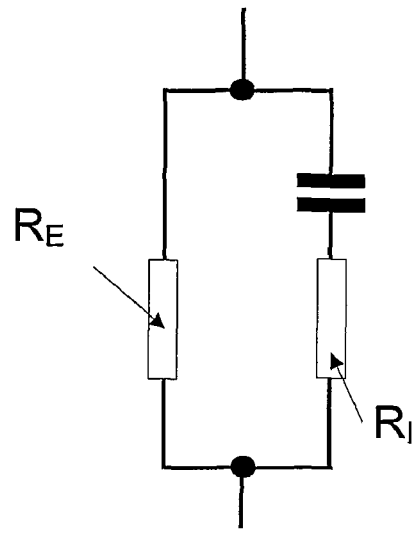
Fig. 3a
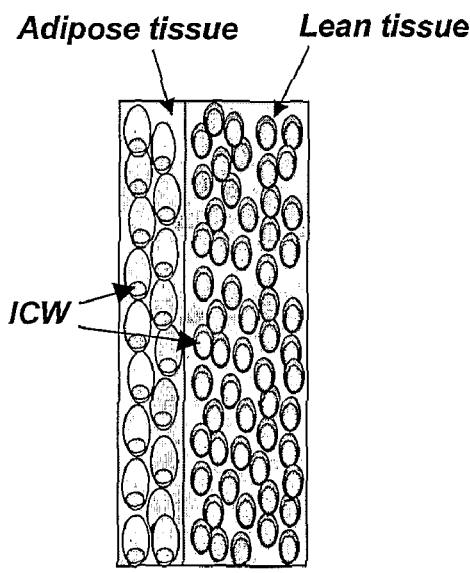
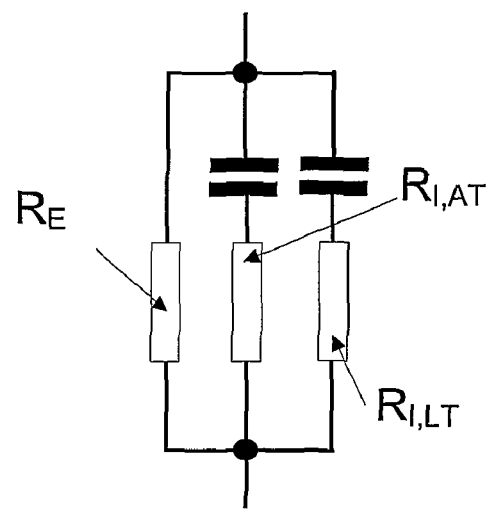
Fig. 3b

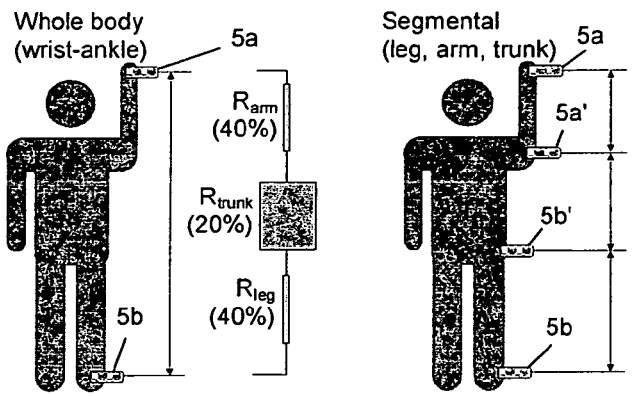
Fig. 6a  Fig. 6b
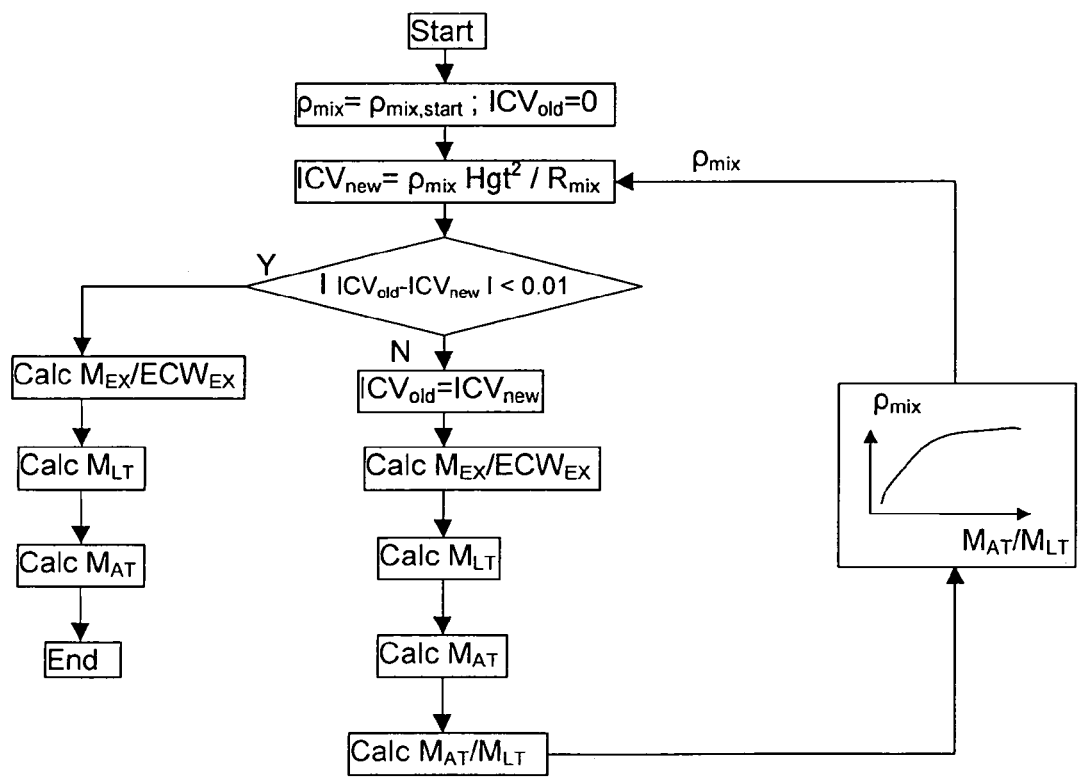
Fig. 7

| Parameter | Value | Description | Unit |
|---|---|---|---|
| $\lambda_{ICW,LT}$ | 0.425 | Volume of intracellular water per unit mass of lean tissue | litres/kg |
| $\lambda_{ICW,AT}$ | 0.154 | Volume of intracellular water per unit mass of adipose tissue | litres/kg |
| $\lambda_{ECW,LT}$ | 0.290 | Volume of extracellular water per unit mass of lean tissue | litres/kg |
| $\lambda_{ECW,AT}$ | 0.096 | Volume of extracellular water per unit mass of adipose tissue | litres/kg |
| $\zeta_{LT}$ | 0.620 | Intracellular volume per unit mass of lean tissue | litres/kg |
| $\zeta_{AT}$ | 0.987 | Intracellular volume per unit mass of adipose tissue | litres/kg |
| $D_{ECW}$ | 1.020 | Density of total extracellular fluid | kg/litres |

Fig. 8

METHOD AND A DEVICE FOR DETERMINING THE HYDRATION AND/OR NUTRITION STATUS OF A PATIENT

This is a nationalization of PCT/EP2004/007023 filed 29 Jun. 2004 and published in English.

The invention relates to the field of monitoring the hydration and/or nutrition status of a patient.

The kidneys carry out several functions for maintaining the health of a human body. First, they control the fluid balance by separating any excess fluid from the patient blood volume. Second, they serve to purify the blood from any waste substances like urea or creatinine. Last not least they also control the levels of certain substances in the blood like electrolytes in order to ensure a healthy and necessary concentration level.

In case of renal failure ingested fluid accumulates in body tissues and the vascular system causing increased stress on the circulatory system. This surplus fluid has to be removed during a dialysis treatment by ultrafiltration of the blood. If insufficient fluid is removed the long term consequences can be severe, leading to high blood pressure and cardiac failure. Cardiac failure itself is many times more likely to occur in dialysis patients and it is thought that states of fluid overload are one of the major contributing factors. Removal of too much fluid is also dangerous since the dialysis patient becomes dehydrated and this invariably leads to hypotension.

The dry weight (for the sake of simplicity the words "weight" and "mass" shall be used synonymously throughout this patent application document—which also is usual practise in the medical field) defines the weight of a patient that would be achieved if the kidneys were working normally. In other words this represents the optimal target weight (or fluid status) which should be achieved in order to minimise cardio-vascular risk. Dry weight has always been an elusive problem in routine clinical practise due to lack of quantitative methods for its assessment. Currently the dry weight problem is approached using indirect indicators like e.g. blood pressure, echocardiographic investigations and subjective information such as X-rays. Furthermore it has been particularly difficult to define a set of conditions which are universally accepted as the dry weight standard.

A promising method to derive the fluid status of a patient involves the use of bioimpedance measurements. A small alternating current is applied to two or more electrodes which are attached to a patient and the corresponding electric potential difference is measured. The various fluid compartments of a human body contribute differently to the measured signals. The use of multiple frequencies allows the water in the intracellular volume (ICV) and the extracellular volume (ECV) to be determined. An example of such a device is described in the international patent application WO 92/19153. However, this document discloses no method regarding how the dry weight of the particular patient can be derived.

U.S. Pat. No. 5,449,000 describes a bioimpedance system also using multiple frequencies to determine water mass in the ECV and ICV. Furthermore certain population dependent data are taken for using and choosing so-called population prediction formulas. The body composition is then analysed by using these formulas and with the help of segmental bio-impedance signals.

The international patent application WO 02/36004 A1 describes a method and a device for deriving the dry weight of a patient with renal failure using a bioimpedance device by extrapolating an excess water volume in the extracellular volume to a condition where there would be no renal failure. By a similar procedure a mass correction term accounting for deviations within healthy human beings and being attributed to certain tissues can be derived.

The international patent application WO 03/053239 A1 discloses a compartmental model which addresses the variation in healthy beings in certain body compartments in order to better separate a mal-hydration volume and other tissue components in particular with the aid of bioimpedance measurements. With such a device information on the nutritional status of a patient can also be obtained.

U.S. Pat. No. 6,615,077 describes an approach for monitoring a dialysis treatment by a bioimpedance device in order to correlate the signals with the progress of the treatment.

A bioimpedance device performing calculations on ICV and ECV water volumes is distributed by Xitron Technologies under the trademark Hydra™. Details about this device are disclosed in the international patent application WO 92/19153. This device relies on an impedance locus model that links the measured impedance values to resistive components simulating the contributions of the water volumes in the intra- and extracellular spaces—ICW and ECW—in order to derive and isolate any values for the ICW and ECW. In the case of the existing device this model is the so-called Hanai model.

By applying the Hanai model the ECW is determined by exploiting the fact that the electrical impedance of body tissue changes when alternating currents of different frequencies are applied to the patient via electrodes. At low frequencies the cell membranes behave as insulators and the applied current passes only through the ECV spaces. At high frequencies the cell membranes become more conductive and thus current passes through both the ICV and ECV spaces. The corresponding impedance locus therefore consists of two parallel branches, the first representing the ECV space by an ohmic resistance $R_E$, the second representing the ICV space by an ohmic resistance $R_I$ and a serially connected capacitance. The water volumes of the respective compartments can then be calculated from the resistance information, based on compartment resistivity constants available from prior studies for which the volumes were also determined by dilution measurements.

The accuracy of methods relying on the thus derived results for the ECW and the ICW, e.g. methods as disclosed in WO 02/36004 A1 or WO 03/053239 A1, then depends on the accuracy of the initial, i.e. the Hanai model. The inventors of the present invention have noticed that certain deficiencies in the accuracy of the results of current bioimpedance methods to assess body water and body tissue have their origin in the constraints of the Hanai model.

Hence there is a need for a bioimpedance method and device that makes use of a refined model by which the water and tissue contributions to the ECV and ICV spaces can be separated more accurately to enable an improved assessment of the body composition of a patient with increased accuracy, providing a better insight into the hydration, nutrition and training status of the patient. It is an object of this invention to provide such a method.

The problem of the invention is solved by a method for determining an intracellular volume ICV of a patient comprising the steps of determining an intracellular electrical resistance $R_{mix}$ of the patient and deriving the intracellular volume ICV using $R_{mix}$ by taking into account that a cell of a first kind of tissue contributes differently to the electrical resistance $R_{mix}$ of the intracellular volume ICV compared with a cell of a second kind of tissue. As an intracellular volume ICV the whole ICV space or just a share like the ICW space or a parameter directly related to these quantities may be considered.

The invention is based on the observation that already small modifications of the Hanai model lead to a considerable improved representation of the physical properties of the tissues of interest, especially as far as lean and adipose tissues are concerned. According to the concept of the invention these modifications in particular concern the intracellular volume.

It is also an object of the invention to provide a device for a non-invasive, accurate and easy to use body compartment assessment. The invention therefore also concerns a device for carrying out the method according to the invention comprising a measurement unit, wherein the measurement unit comprises a bioimpedance device for determining an electrical resistance $R_{mix}$ of an intracellular volume ICV of the patient, and an evaluation unit configured to derive the intracellular volume ICV using $R_{mix}$ by taking into account that a cell of a first kind of tissue contributes differently to the electrical resistance $R_{mix}$ of the intracellular volume ICV compared with a cell of a second kind of tissue.

In a preferred embodiment the evaluation unit is a microprocessor unit which in turn comprises a microprocessor program storage unit, wherein in the microprocessor program storage unit a program for deriving the intracellular volume ICV using $R_{mix}$ by taking into account that a cell of a first kind of tissue contributes differently to the electrical resistance $R_{mix}$ of the intracellular volume ICV compared with a cell of a second kind of tissue is stored.

A computer program product which comprises a storage medium on which a computer program is stored which is to be stored in a device according to the invention for carrying out the methods according to the invention where the evaluation unit comprises a microprocessor storage unit, is also constituting a part of the invention.

Various further embodiments of the invention are subject of the subclaims of the independent claims.

Figure 2:
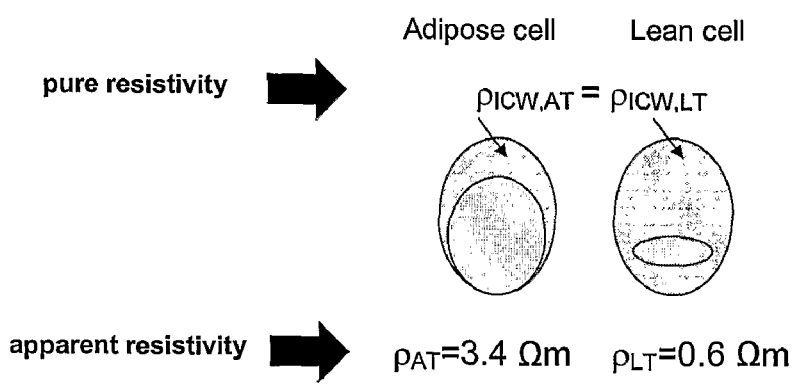
Figure 4:
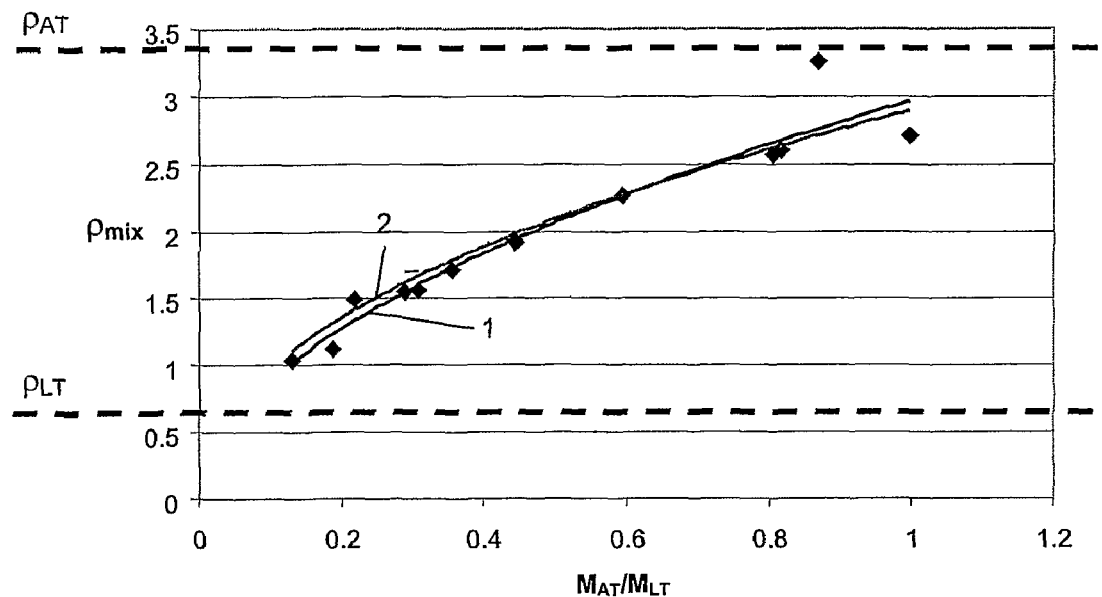
Figure 5:
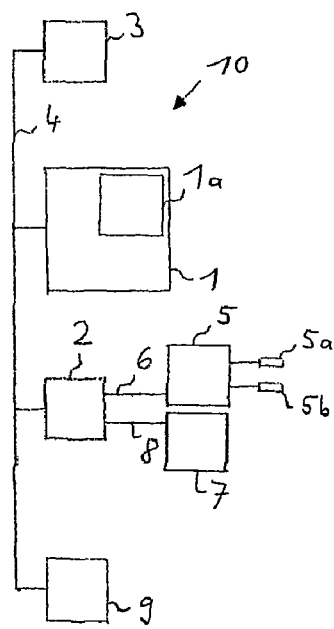

For an improved understanding of the invention, a non-restrictive example will be described with reference to the appended drawings in which FIG. 1 shows a schematic illustration of the three body compartments representing the mal-hydration mass $M_{EX}$, the lean tissue mass $M_{LT}$ and the adipose tissue mass $M_{AT}$, FIG. 2 shows a schematic illustration of a lean and an adipose tissue cell and their influence on the electrical resistivity ρ, FIG. 3a schematically shows the equivalent impedance locus according to the Hanai model, FIG. 3b schematically shows an equivalent impedance locus according to the present invention, FIG. 4 shows an example for the relation between the intracellular mixed resistivity $\rho_{mix}$ and the ratio of the masses $M_{AT}$ and $M_{LT}$ of the adipose and lean tissues, FIG. 5 schematically shows an embodiment of a device for the assessment of the body composition of a patient according to the present invention, FIG. 6a shows a bioimpedance electrode arrangement for whole body bioimpedance measurements, FIG. 6b shows a bioimpedance electrode arrangement for segmental body bioimpedance measurements FIG. 7 shows a graphical overview of an iteration method using the method according to the invention to derive various body compartment masses and FIG. 8 shows a compilation of example values for the various parameters required in the example embodiment for the calculation of the body mass components.

As illustrated in FIG. 1 the human body can be divided into three compartments: an excess fluid or mal-hydration compartment with mass $M_{EX}$, a lean tissue compartment with mass $M_{LT}$ and an adipose tissue compartment with mass $M_{AT}$. For all three compartments the extracellular water (ECW) and intracellular water (ICW) together with other contributions (minerals, proteins, lipids etc.) are also shown in FIG. 1. The excess fluid $M_{EX}$ which mainly accumulates in the ECV space is an indicator of the mal-hydration status of a patient. In a healthy subject $M_{EX}$ would be vanishing. $M_{EX}$ may also have a negative value indicating a hydration status where the patient is overhydrated.

The lean and the adipose tissue are distinguished in the framework of this application by their water contents. The lean tissue mass $M_{LT}$ comprises bones, organs (including blood) and muscles. The majority of the lean tissue has a water content of approx. 72% to 75% while the proportion of bone may lead to some variability in the overall water content. More sophisticated models could be considered to include the influence of bone or other tissues, but for the present purpose such refinements are neglected. Adipose tissue mass $M_{AT}$, on the other hand, is assumed to be largely comprised of lipids and water in the form of fat cells or adipocytes.

In studies of the electrical characteristics of different tissues, it turned out that there is a large scatter in the data of the measured (apparent) resistivity among different subjects. As the composition of intracellular fluid is well known with respect to its electrolyte composition one could conclude that possibly the resistivity of pure fluid is the same regardless of the tissue type. However, it is the non-conducting material contained within the intracellular space that determines the overall or apparent intracellular resistivity. As a result of non-conducting material, current paths are lengthened leading to a non-uniform flux density throughout. Therefore the apparent resistivity will be somewhat higher than the pure intracellular fluid. Fluid in this case refers to an electrolyte solution not containing any organic material such as proteins or lipids. Adipose tissue in particular contains a large quantity of fat and significantly less water, leading to a somewhat higher apparent resistivity than other tissues.

In a first step to properly take into account this inhomogeneity in the cells, it appears to be useful to just distinguish the resistivities of lean cells on one hand and of adipose cells on the other hand (FIG. 2). Therefore, all cells with the exclusion of adipose tissue are assumed to have the same apparent resistivity $\rho_{LT}$. Furthermore, as shown in FIG. 2, the fluid in the cells has the same pure resistivity (denoted by the index "ICW") in all cells.

Although pure intracellular fluid may be similar to any other tissue, fat occupies around 80-90% of adipose intracellular volume. This is illustrated in FIG. 2 by the larger inner circle in the fat tissue cell whereas the remainder of the cells represents the water content of the cells. Therefore the apparent resistivity of adipose tissue will be higher than that of other tissues such as muscle. Current data suggested that the apparent fat resistivity $\rho_{AT}$ is of the order of 3 times higher than the apparent lean resistivity $\rho_{LT}$, consistent with the difference in water content. The values given in FIG. 2 are estimates derived from an analysis made by the inventors.

In the Hanai model one approximates the human body by a first compartment related to the ECV and a second compartment related to the ICV. As far as the electrical properties of such a system are concerned, the cells of the ICV behave as insulators at zero frequency current. The current paths through the still conducting extracellular medium in which the cells are suspended are lenghtened.

When an alternating current is used the cells of the ICV act as further path for the electrical current gaining conductivity with increasing frequency. This situation is illustrated in FIG. 3a. The human body may be represented by tissue consisting of a suspension of cells (ICV) in the ECV fluid space. The electrical properties can be simulated by the impedance locus as also shown in FIG. 3a: the electrical path is split into two paths, the first one acting like an ohmic resistance $R_E$ only and representing the ECV, the second one acting as an ohmic resistance $R_I$ and a serial capacitance representing the ICV.

The basic equation to link the volume V of a compartment like the ECV or ICV of a human body with height Hgt at the time t to the electrical ohmic resistance R and the apparent resistivity ρ is given by Eq. 1:

$$V = \frac{\rho \cdot Hgt^2 \cdot K_B}{R}, \quad (1)$$

wherein $K_B$ is the so-called shape factor accounting for the representation of certain body parts in the measurement path like extremities like arms and legs by an equivalent cylinder model. Since for a particular placement mode of the measurement electrodes $K_B$ is considered to be constant, it may also be absorbed into other terms like a modified resistivity. For simplicity $K_B$ is therefore omitted in the remainder of this specification.

The apparent resistivity of a uniform mixture of electrically conducting and non-conducting material is in turn related to the pure resistivity $\rho_0$ of the conducting material and to the volume ratio c of the non-conducting material by Eq. (2):

$$\rho = \frac{\rho_0}{(1-c)^{3/2}}. \quad (2)$$

In the Hanai model Eqs. (1) and (2) are applied twice, once for the ECV and once for the ICV. Whereas at zero frequency Eqs. (1) and (2) link the ECV resistivity $\rho_E$ with the ECV resistance $R_E$ and c accounts for the non-conducting cells, i.e. the ICV, these equations relate at infinite frequency the total resistivity $\rho_{E+I}$ with the total resistance $R_{E+I}$ for the combined spaces ECV and ICV, c now accounting for non-conducting materials suspended in this volume like lipids, proteins and minerals. By the difference of the total volume from the ECV determined beforehand the ICV is derived.

However, especially for the representation of the ICV, as indicated above, there is a need for improvement. In a limb for example, the bone is surrounded by lean material (mainly skeletal muscle) while the exterior layers consist of adipose tissue otherwise regarded as subcutaneous fat. Hence there are at least two different tissues of primary relevance (the adipose and lean) which have different apparent resistivities as already outlined in the description of FIG. 2.

Therefore the classical electrical model of human body tissue may be modified to characterise at least two paths in the intracellular space. The two tissues may then be taken into account by two parallel conductors. A corresponding impedance locus is shown in FIG. 3b. The two tissues of the ICV are represented by a lean tissue ohmic resistance $R_{I,LT}$ and an adipose tissue ohmic resistance $R_{I,AT}$. Different to FIG. 2 the inner circles in the individual cells now represent the water content in the cells.

The combined apparent resistivity $\rho_{mix}$ of adipose and lean tissue for the ICV is given by:

$$\rho_{mix} = \frac{\rho_{LT} \cdot \rho_{AT} \cdot (V_{LT} + V_{AT})}{\rho_{LT} \cdot V_{AT} + \rho_{AT} \cdot V_{LT}}, \quad (3)$$

wherein $\rho_{LT}$, $\rho_{AT}$ are the apparent resistivities and $V_{LT}$, $V_{AT}$ the volumes of the lean and adipose tissue cells, respectively. By defining a scalar Ψ by Eq. (4)

$$\psi \equiv \frac{V_{AT}}{V_{LT}} \quad (4)$$

$$= \frac{\frac{M_{AT}}{D_{AT}} \cdot \theta_{AT}}{\frac{M_{LT}}{D_{LT}} \cdot \theta_{LT}}$$

$$= \frac{M_{AT}}{M_{LT}} \cdot \frac{D_{LT}}{D_{AT}} \cdot \frac{\theta_{AT}}{\theta_{LT}}$$

$$= \frac{M_{AT}}{M_{LT}} \cdot \chi$$

wherein $M_{AT}$, $M_{LT}$ are the masses and $D_{AT}$, $D_{LT}$ the densities of the adipose and lean tissue compartments and $\theta_{AT}$, $\theta_{LT}$ are the volume fractions of the intracellular tissue volume from the total tissue volume of the adipose and lean tissue compartments, respectively. The scalar χ is dimensionless. Adipose tissue density is around 0.92 kg/liter and muscle density approximately 1.06 kg/liter. Similarly the volume fraction of intracellular fat to total fat volume could well be higher than that of lean tissue. Therefore χ is typically in the range 1.5 to 2. Basically χ is fixed since it is fundamental to the tissue properties of adipose and lean tissue. In practise, however, fluctuations may occur which are due to variations in the shape factor $K_B$ from one individual to another. Care is therefore required for either properly factoring out this factor or for achieving comparable measurement conditions.

Substituting Eq. (4) into Eq. (3) yields $$\rho_{mix} = \frac{\rho_{LT} \cdot \rho_{AT} \cdot (1+\psi)}{\psi \cdot \rho_{LT} + \rho_{AT}}. \quad (5)$$

The factor χ described above is somewhat elusive as it depends on knowledge of volume fractions of intracellular compartments in various tissues. As both muscle and adipose tissue can have variable cell size, it becomes extremely difficult to quantify χ.

In order to address this problem of determining χ, data from dual X-ray absorbitometry (DXA) measurements in a group of healthy subjects were used to provide reference values of fat and lean tissues. The subjects were also measured with bioimpedance in order to determine the corresponding intracellular resistance values. The corresponding data is shown in FIG. 4. The graph denoted by "1" represents a fit to an exponential term as given by Eq. 6:

$$\rho_{mix} = a \cdot \left(\frac{M_{AT}}{M_{LT}}\right)^b, \quad (6)$$

with a=2.9663 Ωm and b=0.5218. The graph denoted by "2" represents a fit to Eq. (5). In FIG. 4 the resistivity values for pure fat and pure lean intracellular tissues are also shown. In the described embodiment of the invention the function according to Eq. (5) or Eq. (6) plays a central role in the application of the new approach to implement routine measurements on patients to derive a mal-hydration water volume and/or the mass/weight of specific compartments like adipose tissue in order to provide a better insight into the hydration and/or nutritional status of a patient.

With the aid of Eqs. (5) or (6) it is possible to derive the true mixed resistivity $\rho_{mix}$ for an individual patient by iteration without requiring an explicit determination of all parameters. Using a typical start value for the ICV, corresponding values for the masses $M_{AT}$ and $M_{LT}$ can be derived that in turn enable a derivation of a new ICV value by using the functions shown in FIG. 4 and thus to derive a new value for the mixed resistivity $\rho_{mix}$. Once sufficient convergence is achieved the true values for $\rho_{mix}$ and ICV are found. In a subsequent step other parameters can finally be calculated. The iteration process itself will be discussed in detail later.

The total ICV can be split into components $ICV_{AT}$ and $ICV_{LT}$. These are linked to the masses $M_{LT}$ of the lean tissue compartment and $M_{AT}$ of the adipose tissue compartment by proportionality constants $\zeta_{LT}$ and $\zeta_{AT}$:

$$ICV = ICV_{LT} + ICV_{AT} = M_{LT}\zeta_{LT} + M_{AT}\zeta_{AT} \qquad (7)$$

The total mass or weight M of the patient is according to FIG. 1:

$$M = M_{LT} + M_{AT} + M_{EX} \qquad (8)$$

Substituting $M_{AT}$ in Eq. (7) with the help of Eq. (8) and solving the resultant equation for $M_{LT}$, Eq. (9) is obtained:

$$M_{LT} = \frac{ICV - \zeta_{AT}(M - M_{EX})}{\zeta_{LT} - \zeta_{AT}}. \qquad (9)$$

Before the lean tissue mass $M_{LT}$ can be derived, the mal-hydration mass $M_{EX}$ has to be calculated. The starting point is the observation that this compartment manifests itself entirely in the ECV space. Taking ECW as the total water volume in the ECV space—wherein ECW can be determined in the usual manner from bioimpedance measurements—, $ECW_{LT}$ as the water volume in the ECV space of the lean tissue compartment and $ECW_{AT}$ as the water volume in the ECV space of the adipose compartment, the mal-hydration extracellular water volume $ECW_{EX}$ is derived by Eq. (10):

$$ECW_{EX} = ECW - ECW_{LT} - ECW_{AT} \qquad (10)$$

Using the following definitions for the volume of intracellular water per unit mass of lean tissue $\lambda_{ICW,LT}$, $$\lambda_{ICW,LT} \equiv \frac{V_{ICW,LT}}{M_{LT}} \qquad (11)$$

for the volume of extracellular water per unit mass of lean tissue $\lambda_{ECW,LT}$, $$\lambda_{ECW,LT} \equiv \frac{V_{ECW,LT}}{M_{LT}} \qquad (12)$$

and for the volume of extracellular water per unit mass of adipose tissue $\lambda_{ECW,AT}$, $$\lambda_{ECW,AT} \equiv \frac{V_{ECW,AT}}{M_{AT}}, \qquad (13)$$

and further introducing the definition $$A = \frac{\lambda_{ECW,LT} - \lambda_{ECW,AT}}{\zeta_{LT} - \zeta_{AT}}, \qquad (14)$$

Eq. (10) can be transformed with the help of Eqs. (8) and (9) into Eq. (15):

$$ECW_{EX} = \frac{ECW - A \cdot ICV + (A \cdot \zeta_{AT} - \lambda_{ECW,AT}) \cdot M}{(1 + (A \cdot \zeta_{AT} - \lambda_{ECW,AT}) D_{ECW})} \qquad (15)$$

wherein $D_{ECW}$ is the density of the extracellular water. Once the mal-hydration volume $ECW_{EX}$ has been determined (and thus the mal-hydration mass $M_{EX}$), the lean tissue mass $M_{LT}$ can be calculated from Eq. (9) and the adipose tissue mass $M_{AT}$ by solving Eq. (8).

After this physical background information an example of the method according to the invention to determine the hydration or nutritional status of a patient is now described with the help of an embodiment of a device according to the invention in detail. Such an embodiment of a device for determining the mal-hydration mass $M_{EX}$ or volume $ECW_{EX}$ of a patient is shown in FIG. 5. The device 10 comprises a microprocessor unit 1 which in turn comprises a microprocessor program storage unit 1a. By means of a link 4 the microprocessor unit 1 is connected to an interface unit 2 and a computer storage unit 3. A program for measuring and determining the masses $M_{EX}$, $M_{LT}$ and/or $M_{AT}$ of a patient at a time t is stored in the microprocessor program storage unit 1a.

The microprocessor program controls the device to determine patient impedance values for two or more frequencies. For the corresponding measurement the device 10 comprises a bioimpedance measurement means 5 which is connected to the interface unit 2 by a link 6. The bioimpedance measurement means 5 can be capable of automatically compensating for influences on the impedance data like contact resistances. An example for such a bioimpedance measurement means 5 is the already mentioned device from Xitron Technologies distributed under the trademark Hydra™.

For the bioimpedance measurement various electrode arrangements are possible. In FIG. 5 only two electrode elements 5a and 5b are attached to the bioimpedance measurement device 5. Each of the electrode units 5a and 5b consists of a current injection electrode and a potential pick up electrode (not shown). By applying the two electrode units 5a and 5b to the wrist and the ankle of a patient, respectively, as outlined in the left part of FIG. 6, the whole body impedance may be determined. Under this electrode configuration the body may be regarded as a combination of several homogenous cylinders, representing trunk, legs and arms. Average contributions of these components to the total impedance are also provided in FIG. 6, mainly resulting from the differing cross-sections of the cylinders.

By using additional electrodes on shoulder and hip, these cylindrical segments may be measured separately, thereby possibly increasing the accuracy of volume determinations. Such a configuration is displayed on the right hand side of FIG. 6. Additional electrode units 5a' and 5b' are attached close to the corresponding shoulder and the hip of the patient enabling a segmental approach to the body elements leg, arm and trunk.

The program stored in the microprocessor storage unit 1a initiates an impedance measurement at at least two given frequencies by recording the corresponding current and voltage signals, both being below critical thresholds so that the device non-invasively probes the patient impedance and can easily be applied by the patient him- or herself without necessarily requiring medical staff.

Returning to the embodiment shown in FIG. 5, the height Hgt of the patient as an anthropometric measure X and the weight or mass M of the patient can be entered into the device 10 via the interface unit 2, e.g. by means of a suitable interface like a keyboard. This may be assisted by a metering and/or weighing means 7 linked to the interface unit 2 by a link 8.

In the embodiment shown in FIG. 5 the interface unit 2 serves as an interface by which the values for Hgt, M and any measured impedance or applied current and voltage values are directly exchanged via the link 4 between the computer storage unit 3, the program stored in the microprocessor program storage unit 1a, the interface 2 and the bioimpedance measurement means 5.

The program stored in the microprocessor storage unit 1a is now—with the help of stored previously established data— processing the stored data in order to determine any contributions of various body tissues to the total body mass.

The whole procedure by which the program progresses in order to derive the various results is summarised in FIG. 7 whereby the parameter values as compiled in FIG. 8 may be used.

As outlined above the ECW value is determined by exploiting the fact that the electrical impedance of body tissue changes when alternating currents of different frequencies are applied to the patient via the electrodes. At low frequencies the cell membranes behave as insulators and the applied current passes only through the ECV spaces, i.e. the ECW volume. At high frequencies the cell membranes become more conductive and thus current passes through both the ICV and ECV spaces. Measurement of the impedance over at least two frequencies, better over a range of frequencies, allows the determination of both the ECW and the ICV.

The ECW is derived from Eq. (1) by taking the resistance R at low or zero frequency to be equal to $R_E$. In the second measurement at a higher frequency the measured impedance R has contributions from both $R_E$ and $R_{mix}$, the latter resistance corresponding to the apparent resistivity $\rho_{mix}$. As $R_E$ is known, $R_{mix}$ can be derived from an impedance locus according to FIG. 3b where $R_{mix}$ accounts for the resultant resistance of both intracellular pathways for the electrical current.

The program is then proceeding with a procedure as outlined in FIG. 7. Taking an average start value for the resistance $\rho_{mix}$, e.g. $\rho_{mix,start}$=0.8 Ωm, and stored values for the resistance $R_{mix}$ and the height Hgt, a start value $ICV_{new}$ is calculated according to Eq. (1). The program then enters an iteration loop which checks the convergence of the data just derived. In this loop the previous value for $ICV_{new}$ is stored as a new value for the parameter $ICV_{old}$ to enable the convergence check at the end of the loop.

With the aid of the value for $ICV_{old}$ the mal-hydration mass $M_{EX}$ or volume $ECW_{EX}$ is derived according to Eq. (15), the lean tissue mass $M_{LT}$ according to Eq. (9) and the adipose tissue mass $M_{AT}$ according to Eq. (8). Having derived a value for $M_{AT}$ and $M_{LT}$, the ratio $M_{AT}/M_{LT}$ is calculated. With the aid of the stored relation $\rho_{mix}(M_{AT}/M_{LT})$, i.e. Eq. (6), a new value for $\rho_{mix}$ is derived. The iteration loop is now closed, and by using the new accomplished value of $\rho_{mix}$ a new value for the intracellular volume $ICV_{new}$ can be calculated according to Eq. (1). Once convergence is established, a consistent value for ICV is found. Then the final values of the various weight components can be calculated, together with any other parameter of interest which can be derived from this parameter value, independent of whether such other parameter was part of the iteration procedure or not.

The result for $M_{EX}$ or $ECW_{EX}$ is finally passed on to an output unit 9 which typically is a display device which displays the result to a user. Further results—independent whether as an intermediate or as an additional result like the mass $M_{AT}$—might add to the informative character of the display.

The compartmental results may be stored in the device to enable a trend analysis including previously derived results. It has also proved useful to smooth the data by deriving weighted average values from the latest and the previous data. For this purpose various algorithms are available in the art to reduce statistical scatter in the data. A useful improvement in the averaging procedure for the current result to be displayed was obtained by giving the latest measurement the highest weight and by decreasing the weight of other, previous measurements with increasing time that has passed since the measurements were taken.

The disclosed device and method according to the invention is hence able to provide for a powerful and more accurate technique for the management of dry weight. In case the weight $M_{AT}$ of the adipose or fat compartment and/or the weight $M_{LT}$ of the lean tissue compartment are also determined the invention is yielding useful further results which allow conclusions about the nutritional status of the patient. This is not dependent on whether the patient is really mal-hydrated or not.

Hence management of any individual is possible, independent of any treatment modality. The invention is particularly applicable for patients which undergo end stage renal failure treatments like hemodialysis, hemofiltration, hemodiafiltration or any forms of peritoneal dialysis (all these treatment modalities are summarised throughout this patent application by the terminology "a dialysis treatment"). A characterisation of hydration status might also be highly desirable within the intensive care setting, since highly abnormal electrolyte- and fluid conditions are frequent for such patients. Furthermore, measurement in virtually any setting where nutrition or fitness parameters are required, including home, pharmacies, medical practices, dialysis units, wards, fitness centres, etc., would be practical.

The invention claimed is:

1. A method for determining an intracellular volume ICV of a patient having lean tissue compartments and adipose tissue compartments comprising the steps of:
   (a) determining an intracellular electrical resistance $R_{mix}$ of the patient by:
      (1) measuring the external cellular electrical resistance $R_E$ of the patient using a first frequency;
      (2) measuring the total electrical resistance R of the patient using a second frequency higher than the first frequency; and
      (3) deriving the intracellular electrical resistance $R_{mix}$ from the results in steps (a)(1) and (a)(2);
   (b) deriving the intracellular volume ICV of the patent by the iterative steps of:
      (1) inputting a typical start value for the intracellular volume as a start value;
      (2) deriving a value for a mass $M_{LT}$ of the lean tissue compartment of the patient;

(3) deriving a value for a mass $M_{AT}$ of the adipose tissue compartment of the patient;

(4) deriving a value for the mixed resistivity $\rho_{mix}$ of the adipose and lean tissue compartments of the patient using reference values for healthy subjects depending on the ratio $M_{AT}/M_{LT}$ of the masses $M_{AT}$ of the adipose tissue compartment and $M_{LT}$ of the lean tissue compartment;

(5) deriving a new value for the intracellular volume ICV using the value of $\rho_{mix}$ derives in step (b)(4) and the value of $R_{mix}$ from step (a); and (6) repeating steps (b)(1)-(b)(5) until sufficient convergence is achieved, using the value from step (b)(5) as a new start value for the step of (b)(1);

(c) outputting the intracellular volume ICV of the patient determined in step (b).

2. The method according to claim 1, further comprising the steps of:
(i) determining at least one anthropomorphic measure X of the patient; and
(ii) incorporating the anthropomorphic measure X in steps (b)(1)-(b)(5) of claim 1.

3. The method according to claim 2, wherein the at least anthropomorphic measure X is the height of the patient.

4. The method according to claim 3, further comprising the step of deriving an extracellular water volume of the patient using the determined $R_E$ value.

5. The method according to claim 4, further comprising the step of deriving a mal-hydration water volume of the patient by using the determined extracellular water volume.

6. The method according to claim 4, further comprising the steps of:
(i) determining the total mass of the patient; and
(ii) deriving the malhydration water volume using the extracellular water volume and the total mass of the patient.

7. A device for practicing the method according to claim 1 comprising:
(1) a measurement unit, wherein the measurement unit includes a bioimpedance device for determining an intracellular electrical resistance $R_{mix}$ of the patient and
(2) an evaluation unit configured to derive the intracellular volume ICV using $R_{mix}$ by taking into account that a cell of a first kind of tissue contributes differently to the electrical resistance $R_{mix}$ of the intracellular volume ICV compared with a cell of a second kind of tissue.

8. The device according to claim 7, wherein the evaluation unit is a microprocessor unit comprising a microprocessor program storage unit.

9. The device according to claim 8, wherein the microprocessor program storage unit comprises a program for deriving the intracellular volume ICV using $R_{mix}$.

10. The device according to claim 8 wherein the program further controls the measurement unit for determining the resistance $R_{mix}$.

11. The device according to claim 7 wherein the device further comprises input means for entering an anthropometric measure X of the patient into the evaluation unit.

12. The device according to claim 7, wherein the measurement unit is further configured to determine an extracellular electrical resistance $R_E$ of the patient and the evaluation unit is further configured to derive the extracellular water volume ECW using $R_E$.

13. The device according to claim 12, wherein the evaluation unit is further configured to derive a malhydration water volume $ECW_{EX}$ using the extracellular water volume ECW.

14. The device according to claim 13, wherein the device further comprises input means for entering the total mass M of the patient into the evaluation unit and the evaluation unit is configured to derive the malhydration water volume $ECW_{EX}$ using M.

15. The device according to claim 7, wherein the evaluation unit is configured to derive the masses $M_{AT}$ of the first type of tissue and $M_{LT}$ of the second type of tissue of the patient.

16. The device according to claim 15, wherein the first type of tissue is adipose tissue and the second type of tissue is lean tissue.

17. The device according to claim 16, wherein lean tissue is defined as the tissue of the patient which is not adipose tissue.

18. The device according to claim 7, wherein the device further comprises an output unit linked to the evaluation unit for outputting data derived from the evaluation unit.

19. The device according to claim 18, wherein the output unit displays the data derived from the evaluation unit.

20. A computer program product comprising a storage medium on which a microprocessor program according to claim 9 is stored.

* * * * *